(12) United States Patent
Bächler et al.

(10) Patent No.: US 6,579,453 B1
(45) Date of Patent: *Jun. 17, 2003

(54) APPARATUS FOR SEPARATING MAGNETIC PARTICLES

(75) Inventors: Guido Bächler, Berkeley, CA (US); Patrick Hunziker, Emmenbrücke (CH); Werner Rey, Ebikon (CH)

(73) Assignee: Roche Diagnostics Corporation, Indianapolis, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,663

(22) Filed: Sep. 29, 1998

(30) Foreign Application Priority Data

Sep. 29, 1997 (EP) .............................. 97116857

(51) Int. Cl.⁷ .................................................. B03C 1/06
(52) U.S. Cl. ...................................... 210/222; 209/222
(58) Field of Search .................. 210/695, 222, 210/324; 435/173.1, 173.9; 209/217, 232, 222, 39; 366/273, 274

(56) References Cited

U.S. PATENT DOCUMENTS

| | | | |
|---|---|---|---|
| 3,752,443 A | | 8/1973 | Lichtenstein |
| 4,911,555 A | * | 3/1990 | Saffer et al. |
| 5,200,071 A | * | 4/1993 | Spiegel |
| 5,670,329 A | | 9/1997 | Oberhardt |
| 5,705,062 A | * | 1/1998 | Knobel |
| 5,770,461 A | * | 6/1998 | Sakazume et al. |
| 6,033,574 A | * | 3/2000 | Siddiqi |

FOREIGN PATENT DOCUMENTS

| | | |
|---|---|---|
| DE | 44 29 155 | 2/1996 |
| EP | 0 691 541 | 1/1996 |
| EP | 0 712 000 | 5/1996 |
| WO | 93 08919 | 5/1993 |
| WO | 96 31781 | 10/1996 |
| WO | 96/31781 | * 10/1996 |

OTHER PUBLICATIONS

Derwent Abstract of DE 44 29 155, Accession No. 96–117621/199613.
Derwent Abstract of WO 96/31781, Accession No. 96–443978/199645.
Derwent Abstract of EP 0 691 541, Accession No. 96–059847/199607.

* cited by examiner

Primary Examiner—W. L. Walker
Assistant Examiner—David Sorkin
(74) Attorney, Agent, or Firm—Gibbons, Del Deo, Dolan, Griffinger & Vecchione

(57) ABSTRACT

Apparatus is disclosed for separating magnetic particles in suspension in a liquid contained in a reaction vessel of the type used in an automatic apparatus for processing biological samples. The apparatus comprises a rotatable carrier holding an array of magnet elements positioned on the carrier at different distances from the rotation axis of the carrier and at different azimuth angles. The carrier and the array of magnet elements can be positioned at a plurality of predetermined angular positions and heights.

17 Claims, 18 Drawing Sheets

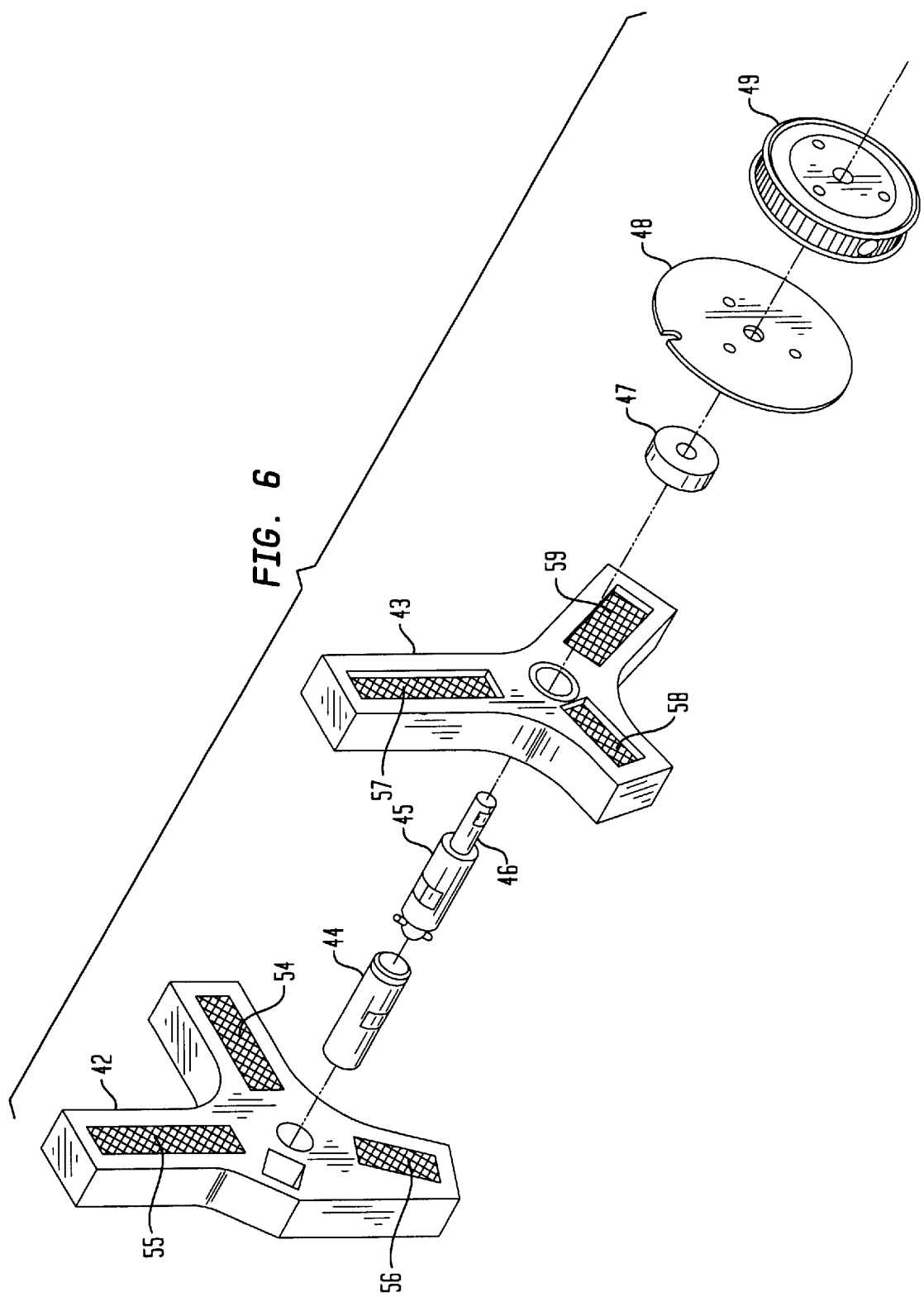

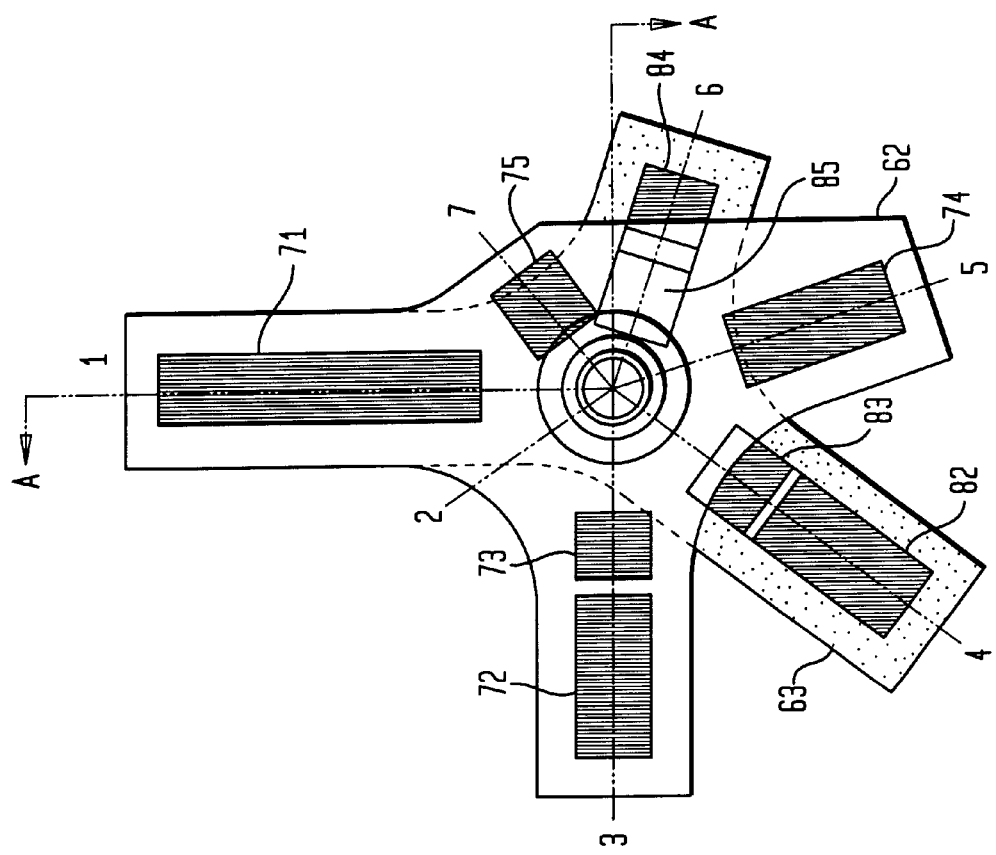
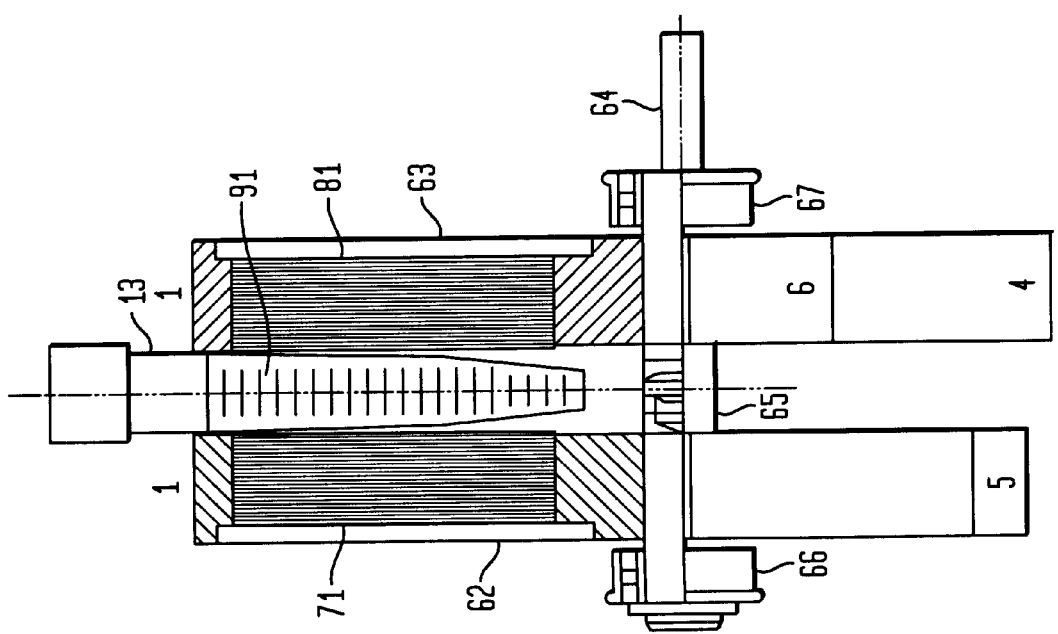

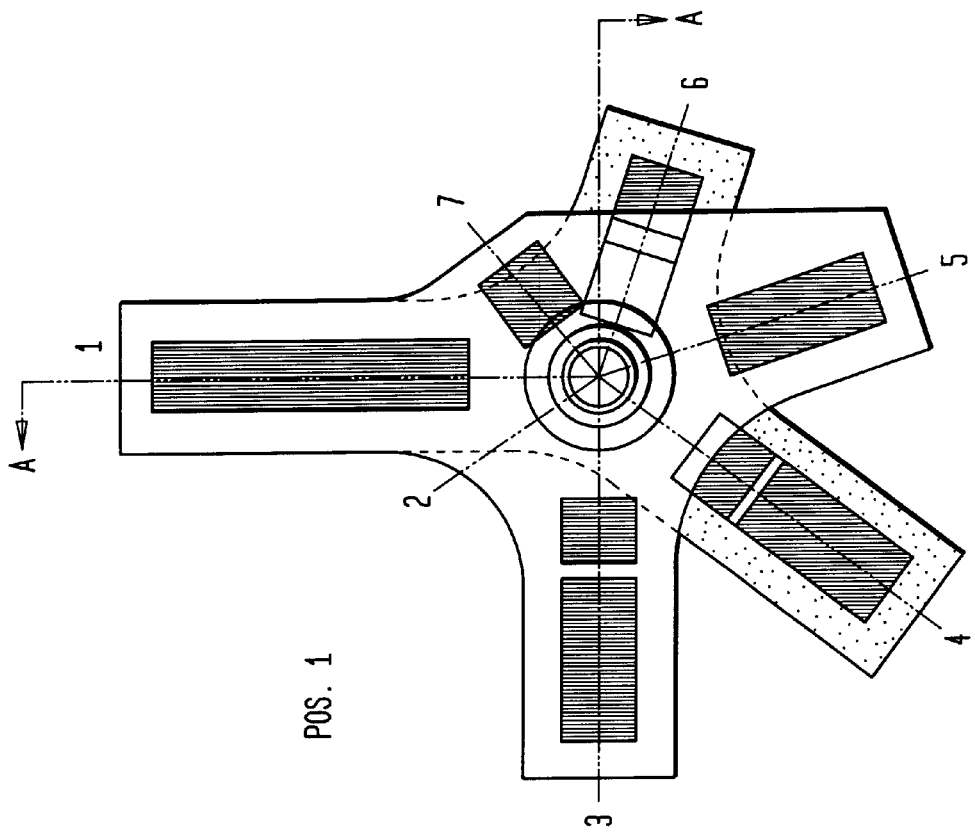
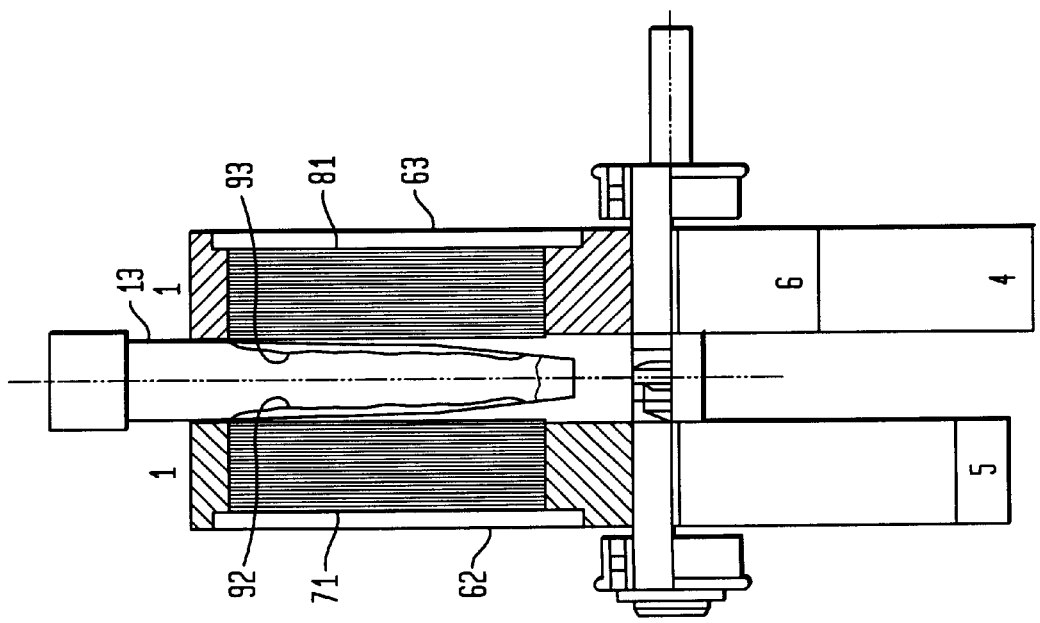

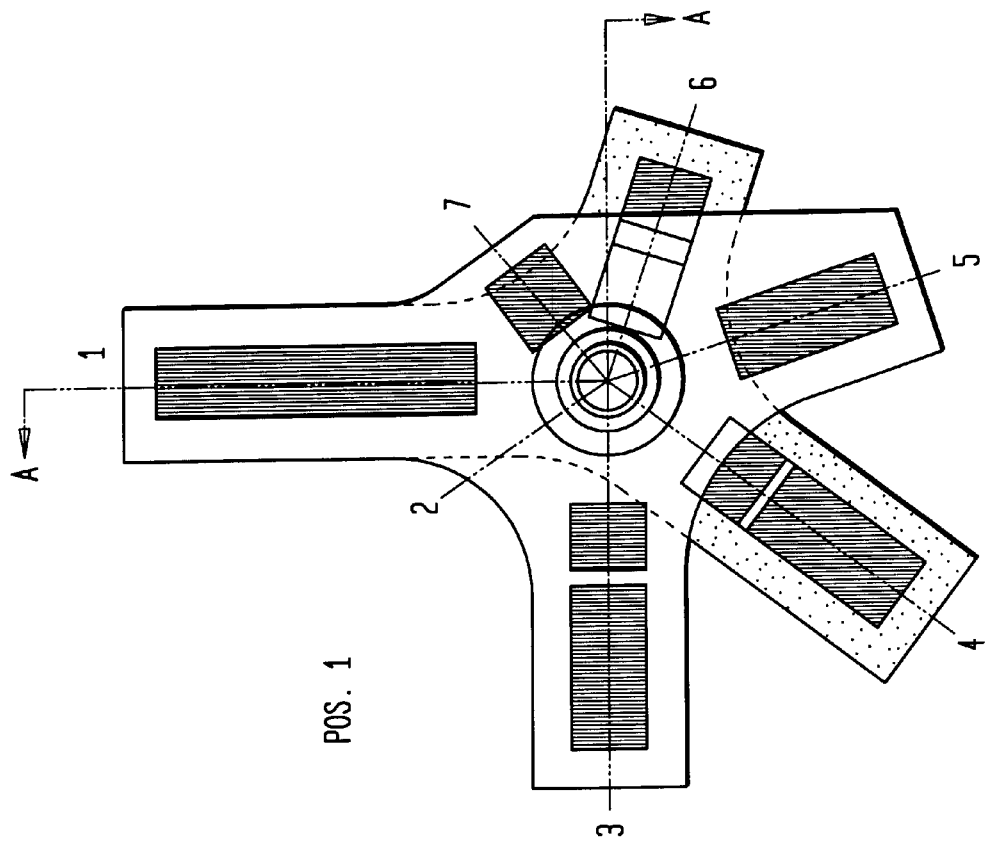
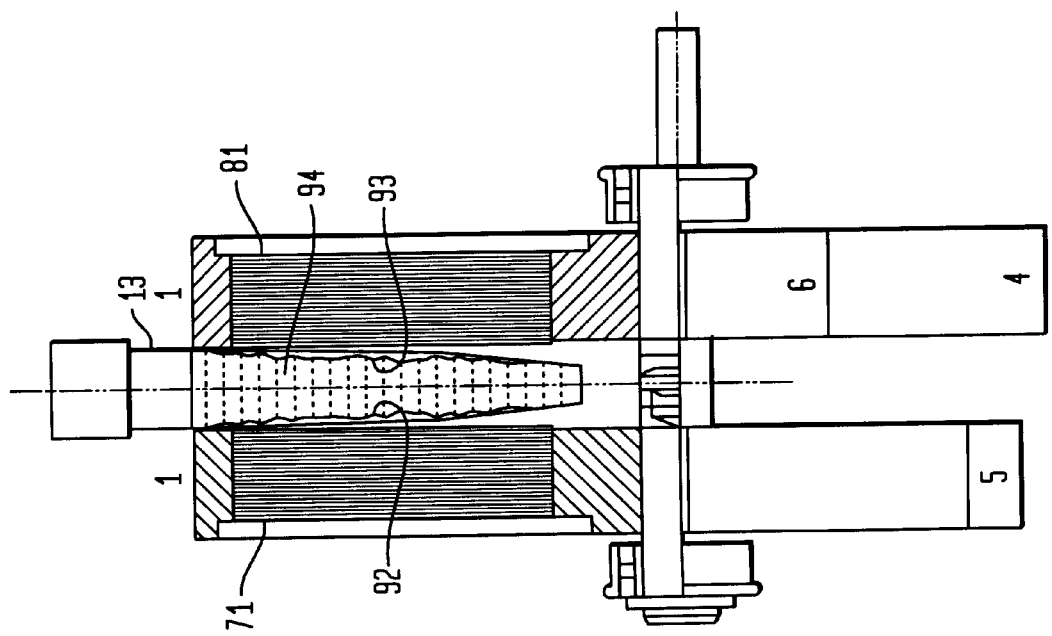

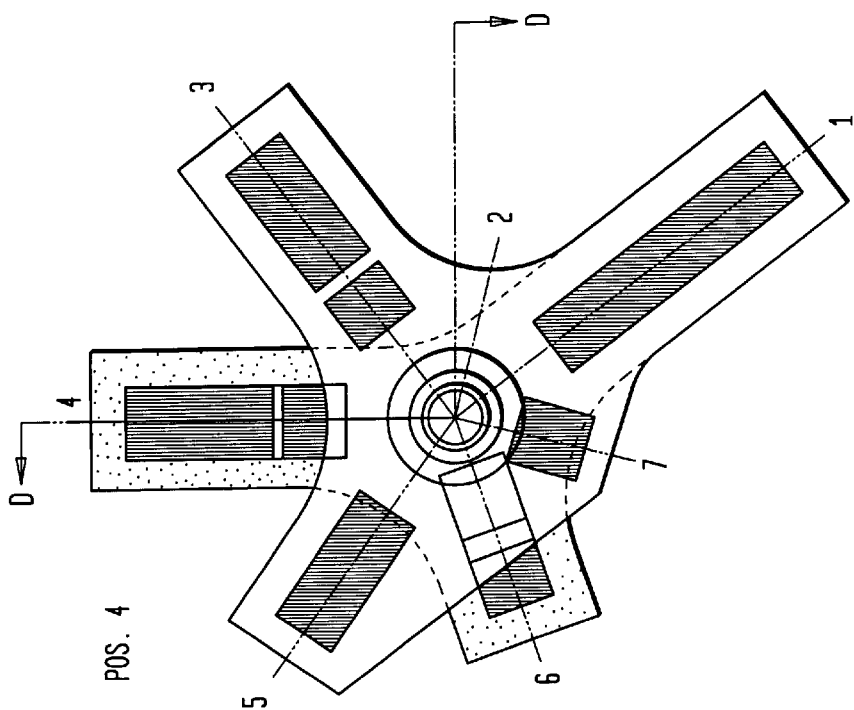
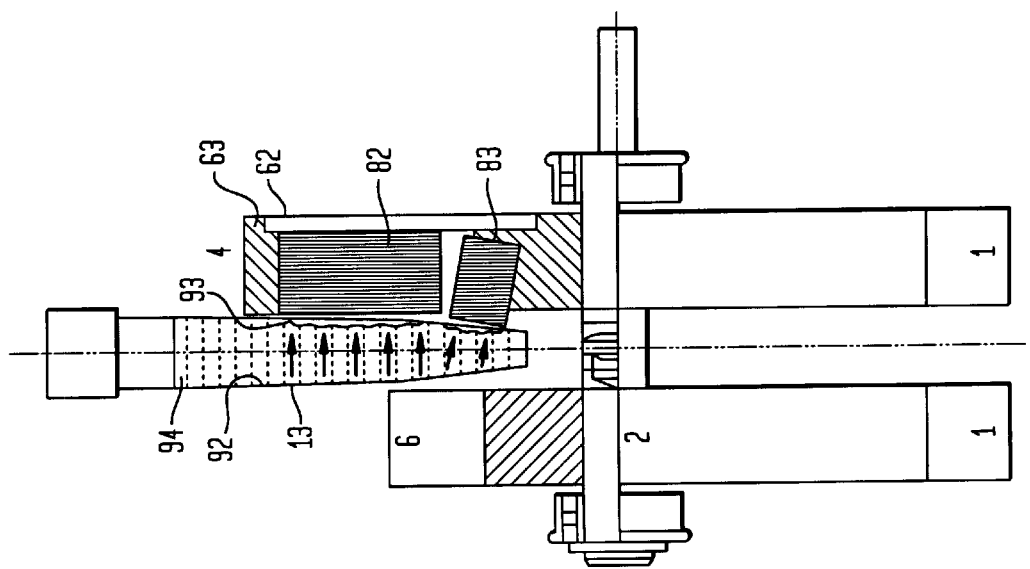

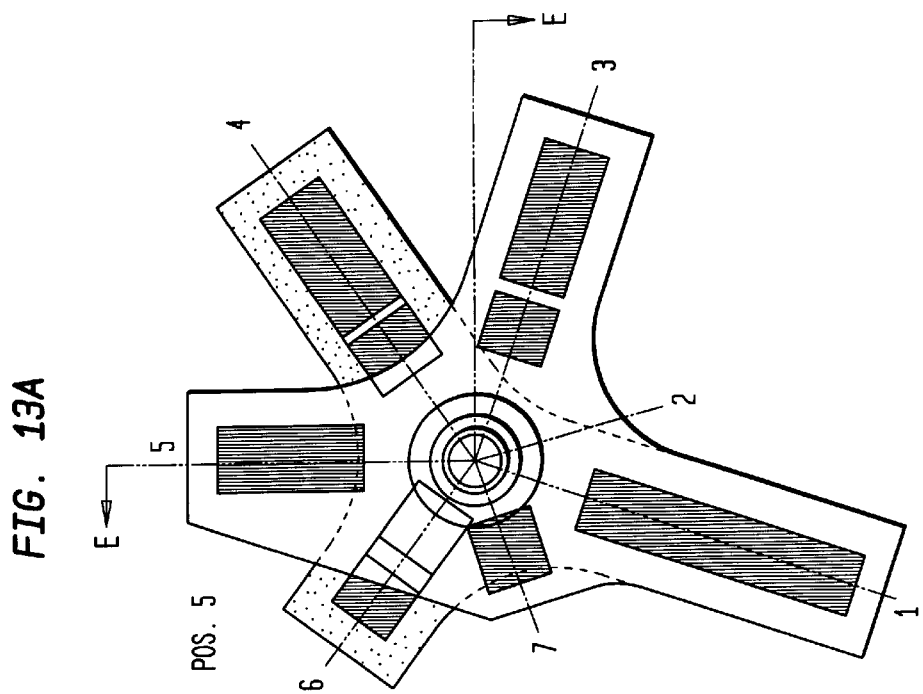
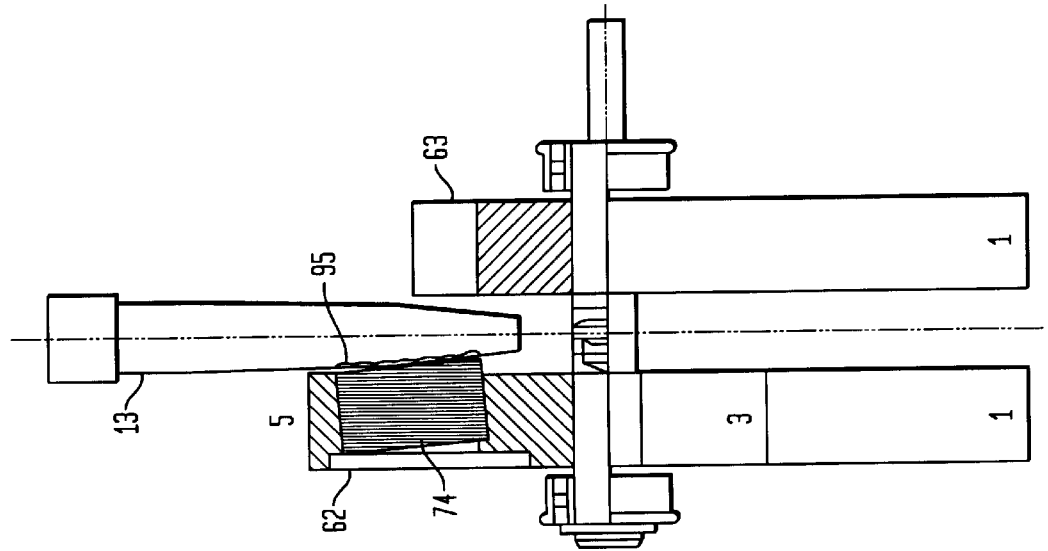

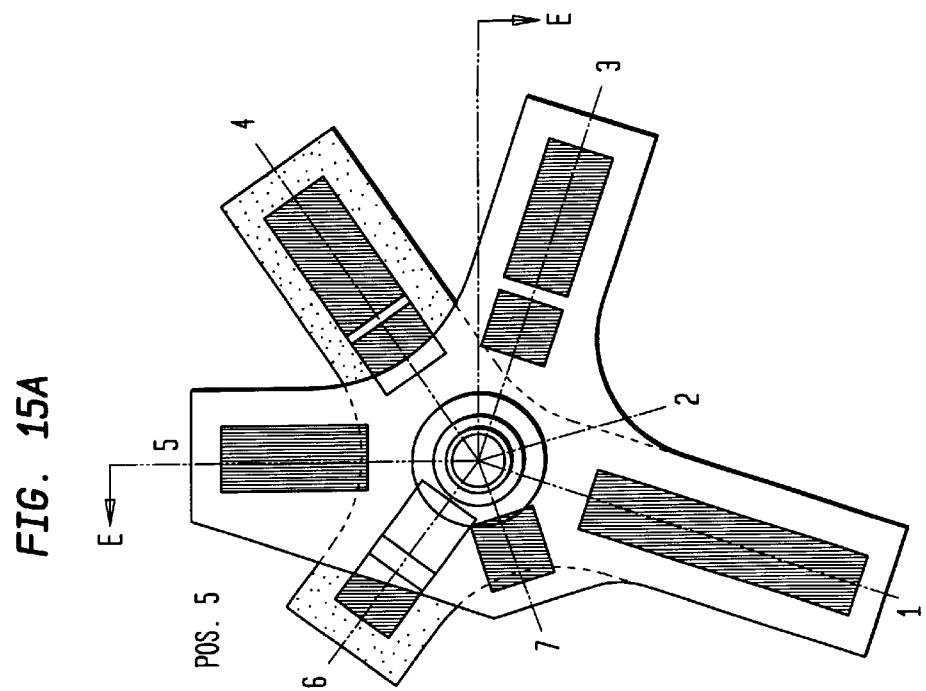
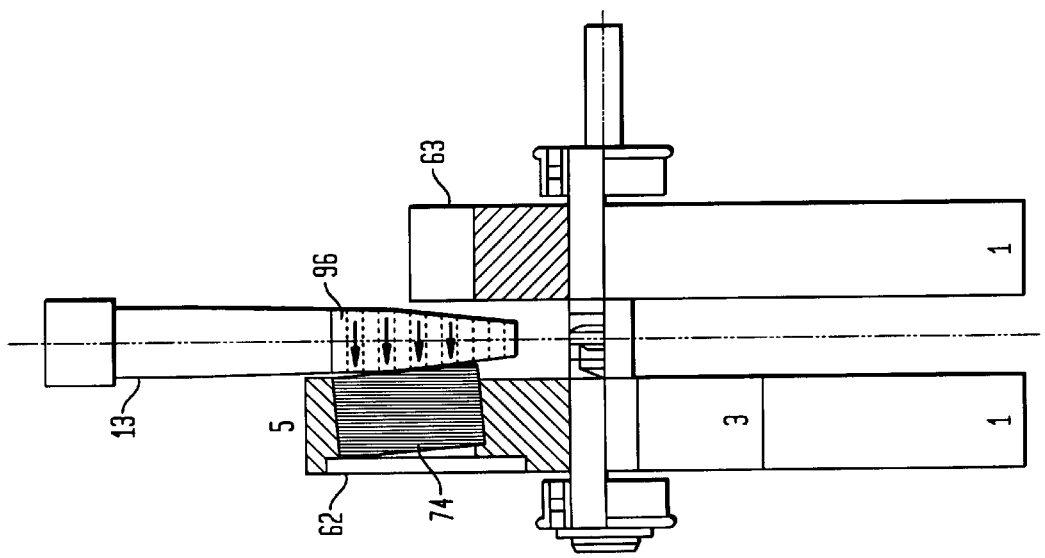

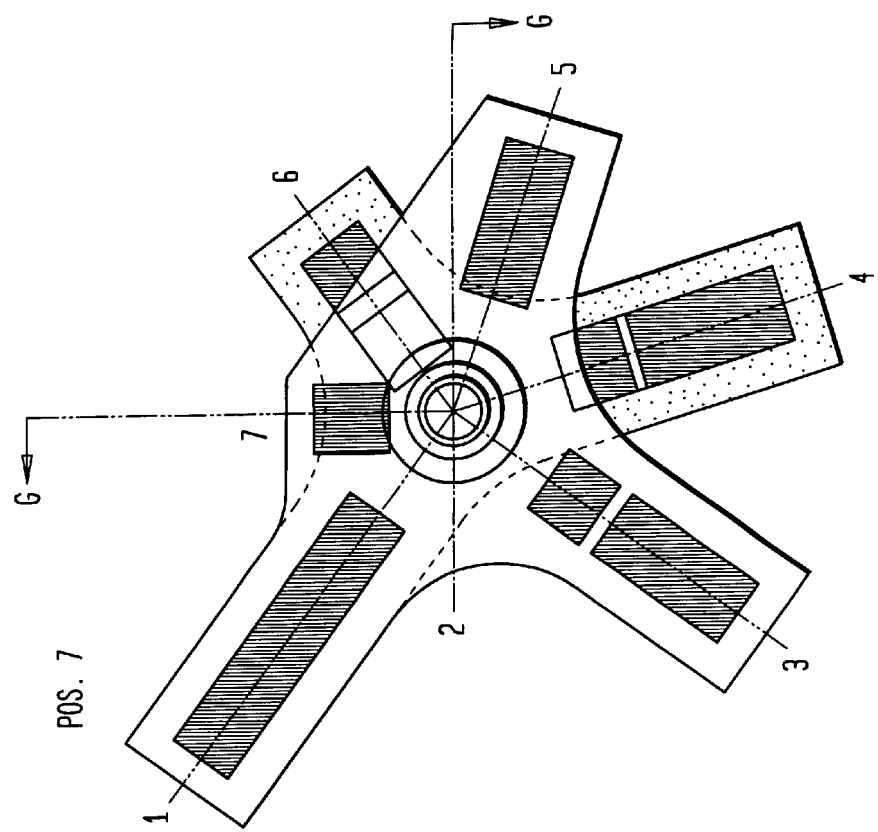
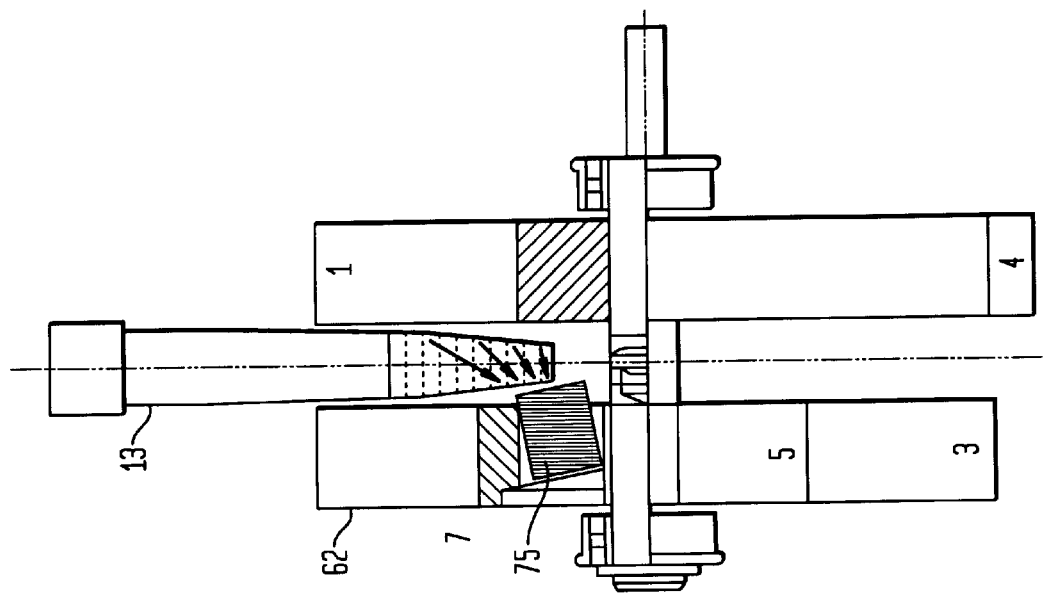

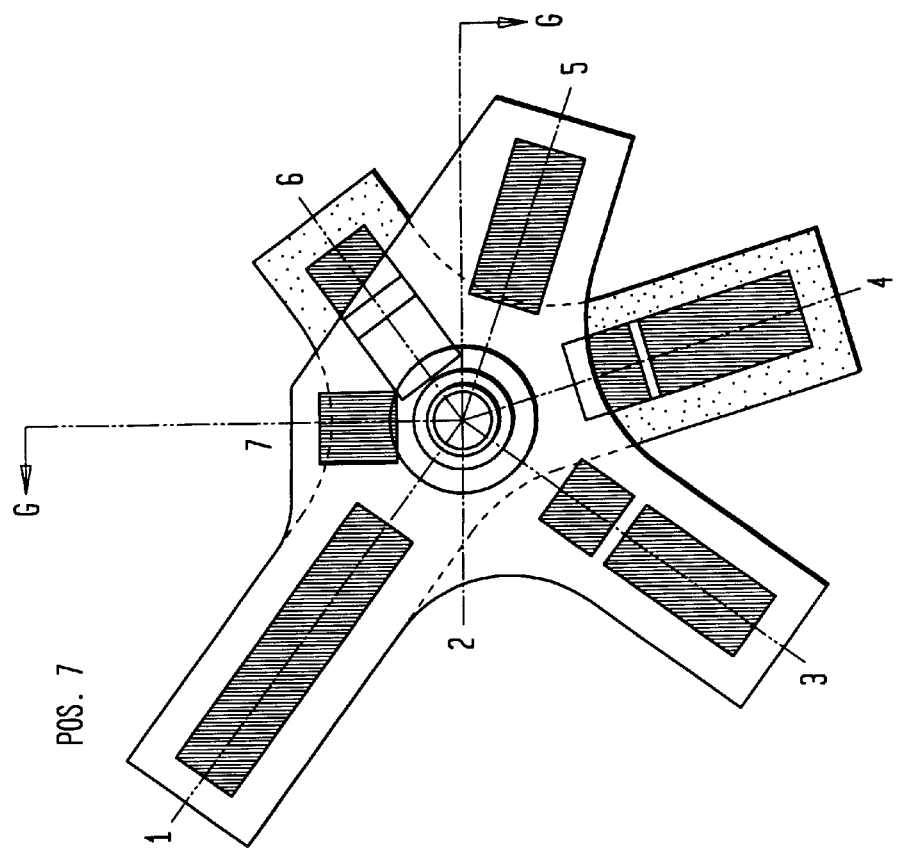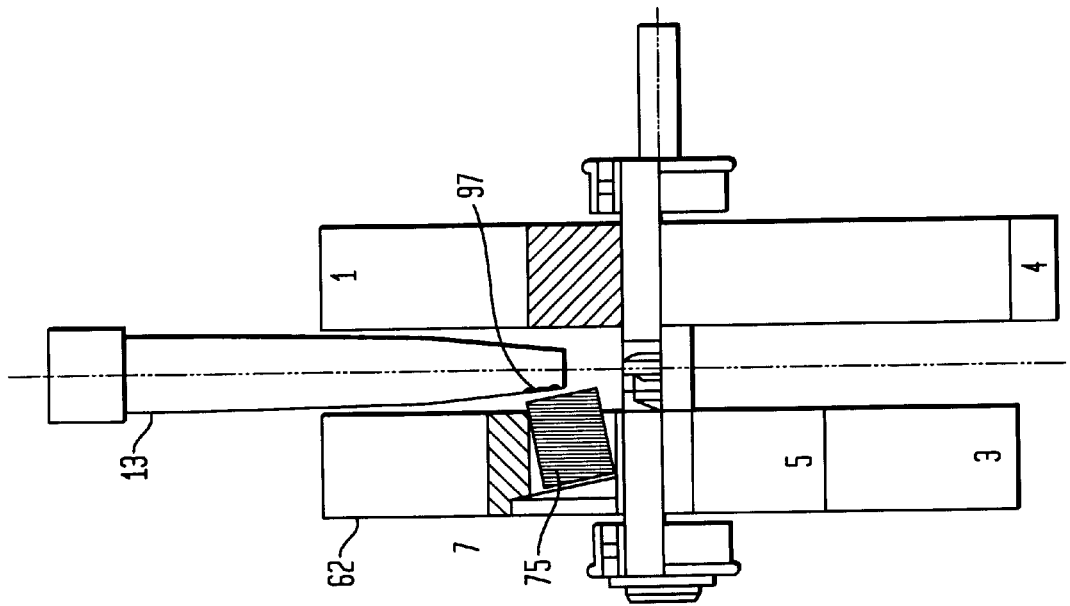

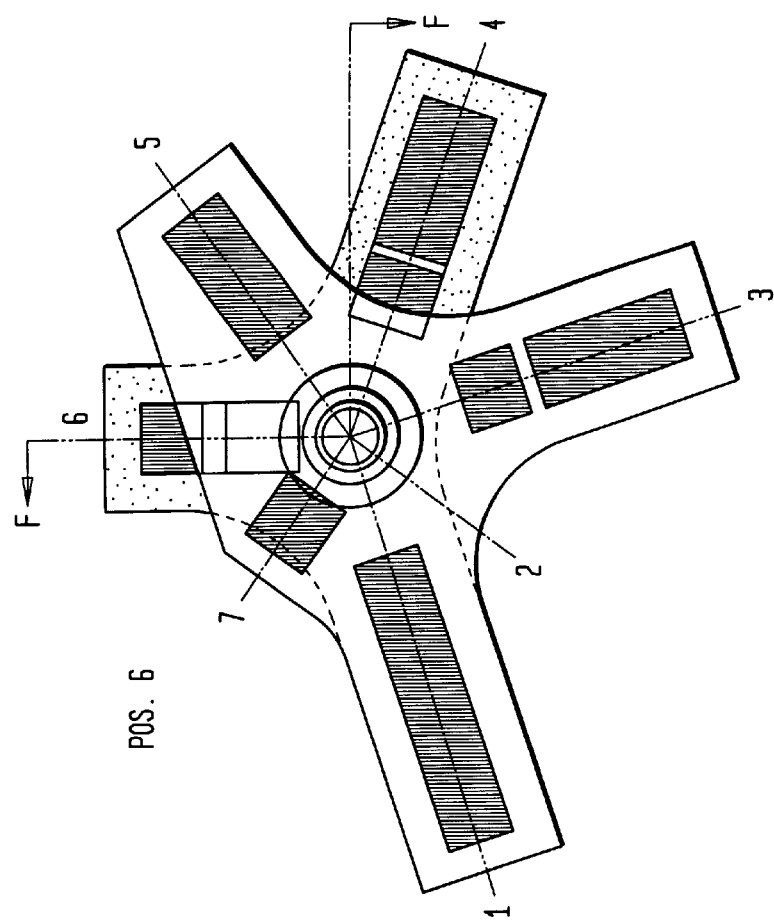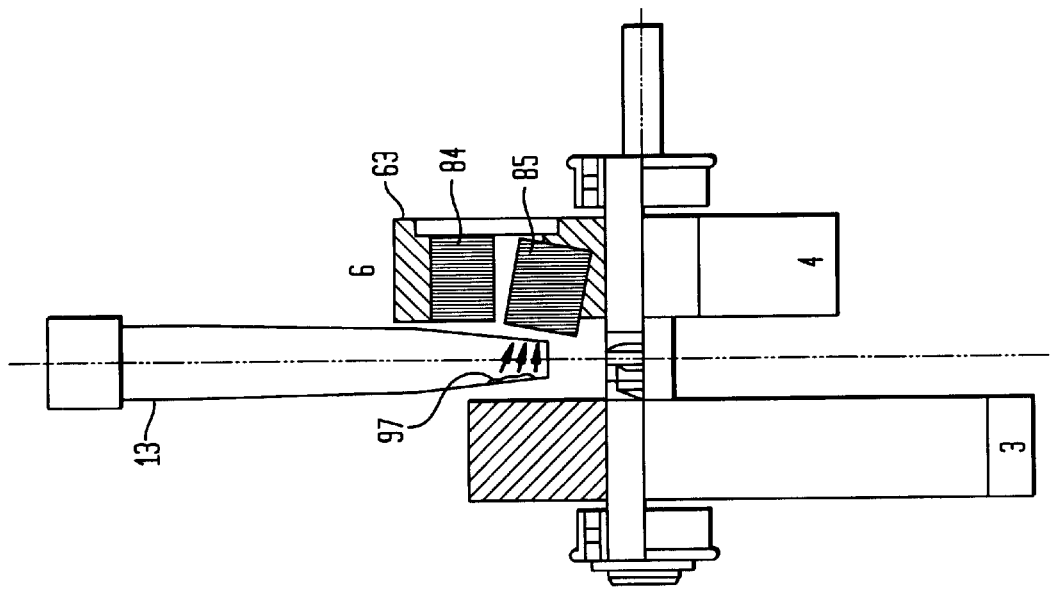

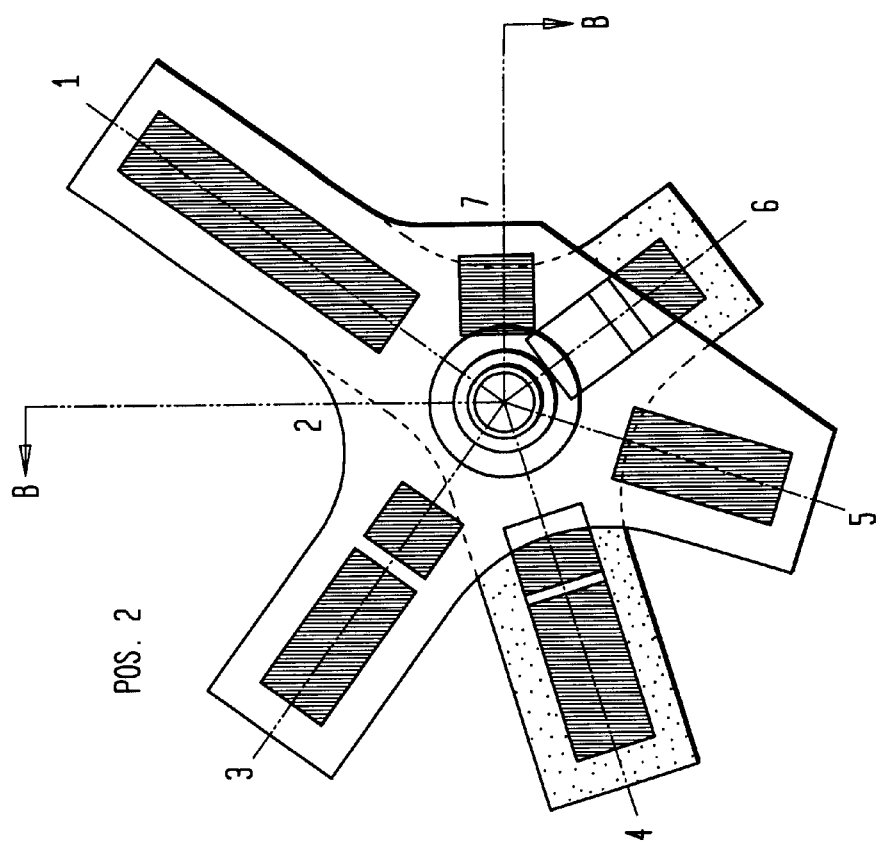
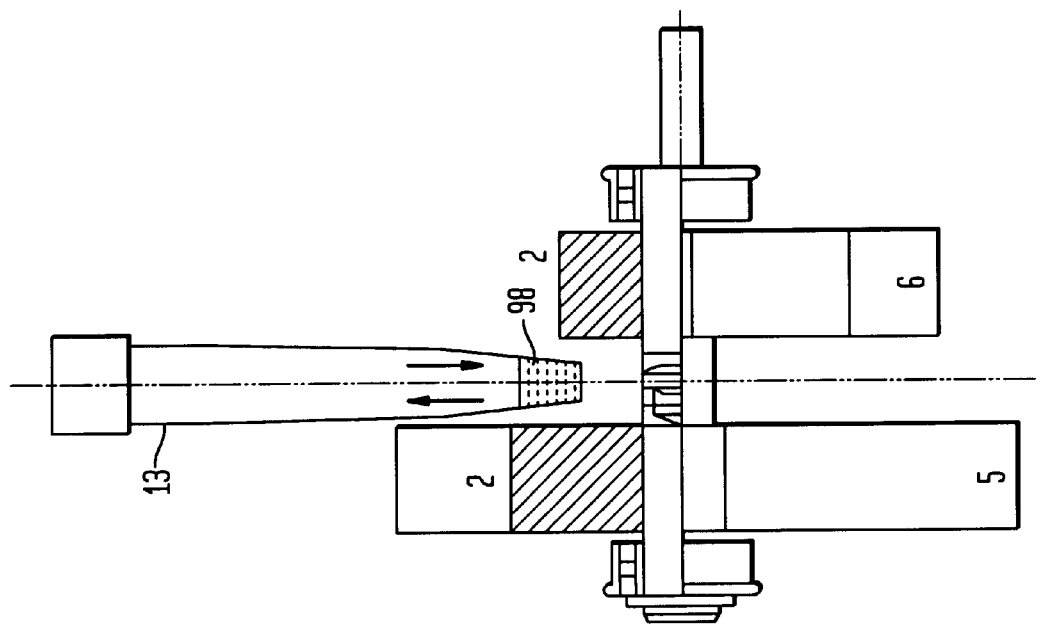
FIG. 21A
FIG. 21B

APPARATUS FOR SEPARATING MAGNETIC PARTICLES

The invention relates to an apparatus for separating magnetic particles in suspension in a liquid contained in a reaction vessel of the type used in an automatic apparatus for processing biological samples, said processing including introducing a sample and one or more reagents into the reaction vessel.

Magnetic particles are used as solid phase for performing some diagnostic assays, e.g. immunoassays. Such assays comprise magnetic particles in suspension in a reaction solution contained in a reaction vessel. When the assay is conducted, it may be necessary to separate the magnetic particles from the liquid contained in the reaction vessel. In known apparatus this is usually done by attracting the magnetic particles to the walls of the reaction vessel by means of magnets positioned close to the outer side wall of the reaction vessel and by extracting the liquid from the reaction vessel by suitable means. This separation step is usually followed by a so called washing step in which the magnets are withdrawn to eliminate the magnetic force which held the magnetic particles on the inner wall of the reaction vessel during the previous separation step and fresh liquid pipetted into the reaction vessel in a way suitable to cause resuspension of the magnetic particles in the liquid contained in the reaction vessel.

A disadvantage of known apparatuses for performing the above-described separation step is that the relative movement of the magnet or magnets with respect to the reaction vessel is a translational movement and this has the disadvantage that the magnetic force exerted on the magnetic particles cannot be quickly removed and this causes an undesirable delay of the resuspension step. According to WO-A-96/31781 this latter disadvantage can be overcome by moving the magnet or magnets along a circular path.

In known apparatuses for performing the above-described separation step, the magnet or magnets used therefor are positioned always at the same position. This has the disadvantage that the separation step can be carried out properly and fast enough only for a limited variation range of the amount of the reaction solution contained in the reaction vessel. Outside that limited range the separation step is too slow.

A main object of the invention, therefore, is to provide an apparatus to overcome the above mentioned disadvantages of prior art apparatuses.

A further object of the invention is to provide an apparatus which is also suitable for performing not only the above described separation step, but also a washing step.

According to the invention, this problem is solved by an apparatus which comprises a) a carrier holding an array of magnet elements; said carrier being rotatable about a rotation axis, b) said array of magnet elements comprising a first magnet element and at least a second magnet element, said first and second magnet elements being positioned on the carrier at different distances from the rotation axis and the centers of the first magnet element and of the second magnet element lying on radii located at different azimuth angles, the carrier and the array of magnet elements being so configured and dimensioned that by rotation of the carrier the first magnet element can be positioned close to the external surface of a side wall of the reaction vessel on one side thereof and at a first predetermined height with respect to the bottom of the reaction vessel, and that by further rotation of the carrier of a predetermined angle the at least second magnet element can be positioned close to said external surface of the side wall of the reaction vessel at a second predetermined height with respect to the bottom of the reaction vessel, said second predetermined height being different from said first predetermined height, and c) means for selectively positioning said carrier and thereby said array of magnet elements at a plurality of predetermined angular positions.

The main advantage of the apparatus according to the invention as compared with the prior art is that it enables a fast separation of magnetic particles contained in suspension in a reaction solution contained in a reaction vessel. This fast separation is obtained by rapid positioning of magnets close to the reaction vessel and at a plurality of selected heights with respect to the bottom of the reaction vessel. The height at which a magnet is positioned at a given point of time being selected according to a processing step to be carried out in the reaction vessel and/or according to the amount of reaction solution contained in the reaction vessel. This permits optimum adaptation of magnetic particle separation step to the process step being carried out in the reaction vessel.

A further advantage of the apparatus according to the invention is that it also enables rapid removal of magnets positioned close to the reaction vessel during a separation step. This rapid removal reduces the time interval necessary to obtain a resuspension of the magnetic particles in liquid contained in the reaction vessel.

A preferred embodiment of the apparatus according to the invention is characterized in that it comprises a) a first carrier holding a first array of magnet elements; said first carrier being rotatable about a first rotation axis, b) a second carrier holding a second array of magnet elements; said second carrier being rotatable about a second rotation axis, c) said first and second carriers being so connected with each other that rotation of one the carriers through a predetermined angle causes rotation of the other carrier of the same angle, d) each of said first and second arrays of magnet elements comprising a first magnet element and at least a second magnet element, said first and second magnet elements being positioned on the carrier at different distances from the rotation axis of the respective carrier of the array of magnet elements and the centers of the first magnet element and of the second magnet element lying on radii located at different azimuth angles, the carriers and the arrays of magnet elements being so configured and dimensioned that by rotation of the carriers, one or more of the magnet elements of the first array of magnet elements can be positioned close the external surface of the side wall of the reaction vessel on one side thereof and/or one or more of the magnet elements of the second array of magnet elements can be positioned close to the external surface of the side wall of the reaction vessel on the opposite side thereof, and that by further rotation of the carriers through a predetermined angle other magnet element or elements of the first array of magnet elements can be positioned close to the external surface of the side wall of the reaction vessel on one side thereof and/or other magnet element or elements of the second array of magnet elements can be positioned close to the external surface of the side wall of the reaction vessel on the opposite side thereof, and e) means for selectively positioning said first and second carriers and thereby said first and second arrays of magnet elements at a plurality of predetermined angular positions.

The advantage of this preferred embodiment is that the combined effect of magnets positioned on opposite sides of a reaction vessel makes it possible to obtain a fast separation of magnetic particles contained in suspension in a reaction solution contained in a reaction vessel, even in a wide vessel.

A further preferred embodiment of the apparatus according to the invention comprises a) a first carrier holding a first array of magnet elements; said first carrier being rotatable about a first rotation axis, b) a second carrier holding a second array of magnet elements; said second carrier being rotatable about a second rotation axis, c) said first and second carriers being so connected with each other that rotation of one the carriers of a predetermined angle causes rotation of the other carrier of the same angle, d) each of said first and second arrays of magnet elements comprising a first magnet element and at least a second magnet element, said first and second magnet elements being positioned on the carrier which holds the array at different distances from the rotation axis of the carrier and the centers of the first magnet element and of the second magnet element lying on radii located at different azimuth angles, said first and second carrier and the arrays of magnet elements they hold being so configured and dimensioned that by rotation of the carriers, one or more of the magnet elements of the first array of magnet elements can be positioned close to the external surface of the side wall of the reaction vessel on one side thereof, and that by further rotation of the carriers of a predetermined angle, one or more of the magnet elements of the second array of magnet elements can be positioned close to the external surface of the side wall of the reaction vessel on the opposite side thereof, whereby one or more magnet elements are alternatively positioned close to the external surface of the side wall of the reaction vessel either on one side or on the opposite side thereof, simultaneous positioning of magnet elements close to the external surface of the side wall of the reaction vessel on both sides thereof being excluded, and e) means for selectively positioning said first and second carriers and thereby said first and second arrays of magnet elements at a plurality of predetermined angular positions.

The advantage of this preferred embodiment is that it enables a washing step, that is a washing of the magnetic particles in suspension in a liquid, e.g. water, contained in a reaction vessel, by alternatively positioning a magnet or an array of magnet elements either on one side of the vessel or on the opposite side of the vessel, and thereby causing migration of the magnetic particles through the liquid from one side of the vessel to the opposite side thereof, the sense of this migration being reversed by changing the side on which a magnet is positioned close to the vessel.

Another preferred embodiment of the apparatus according to the invention is characterized in that each of the magnet elements of said array or arrays of magnet elements comprises one or more magnets having the same width and the same azimuthal position on the carrier of the array.

A further preferred embodiment of the apparatus according to the invention is characterized in that the axis of rotation of the carrier, respectively of each of the carriers, intersects with the length axis of the reaction vessel at a point located below the bottom of the reaction vessel.

A further preferred embodiment of the apparatus according to the invention comprising a first and a second rotatable carrier is characterized in that the axis of rotation of the carriers form an angle which is in the range between 170–175 degrees. In an alternative preferred embodiment the carriers have a common axis of rotation.

A further preferred embodiment of the apparatus according to the invention is characterized in that said means for selectively positioning said carrier or carriers are apt to position said carrier or carriers at predetermined angular positions which are selected according to a processing step to be carried out in that reaction vessel and/or according to the amount of liquid in the reaction vessel.

A further preferred embodiment of the apparatus according to the invention is characterized in that said plurality of predetermined angular positions include one position at which no magnet element of said array or arrays of magnet elements is located close to any external surface of the reaction vessel.

Examples of embodiments of an apparatus according to the invention are described below with reference to the accompanying drawings wherein:

FIG. 6 is an exploded view of magnet array carriers of a third embodiment of an apparatus according to the invention.

FIG. 7a shows a front view of a fourth embodiment of an apparatus according to the invention.

FIG. 7b shows a side elevation view including a cross-section through planes indicated by lines A—A of the apparatus according to FIG. 7a and shows also a reaction vessel 13.

FIGS. 8a and 8b, etc. up to FIGS. 21a and 21b show the carriers of arrays of magnet elements shown by FIGS. 7a and 7b in a plurality of angular positions and also illustrate different processing steps carried out in the reaction vessel 13.

Several embodiments of an apparatus according to the invention are described hereinafter. These embodiments each comprise two rotatable carriers of magnet arrays. Simplified embodiments comprising only one rotatable carrier of a magnet array are however within the scope of the invention.

First Embodiment

A first embodiment of an apparatus according to the inventions is shown by FIGS. 1 to 4. These figures show an apparatus for separating magnet particles in suspension in a liquid contained in a reaction vessel 13 of the type used in an automatic apparatus for processing biological samples. Such a processing includes introduction of a sample and one or more reagents into reaction vessel 13, and positioning said reaction vessel in a predetermined stationary position by any positioning means such as vessel aligner 30. The apparatus shown by FIGS. 1 to 4 comprise a first carrier 11 holding a first array of magnet elements 14–19. Carrier 11 is rotatable about a rotation axis 15.

Figure 1:
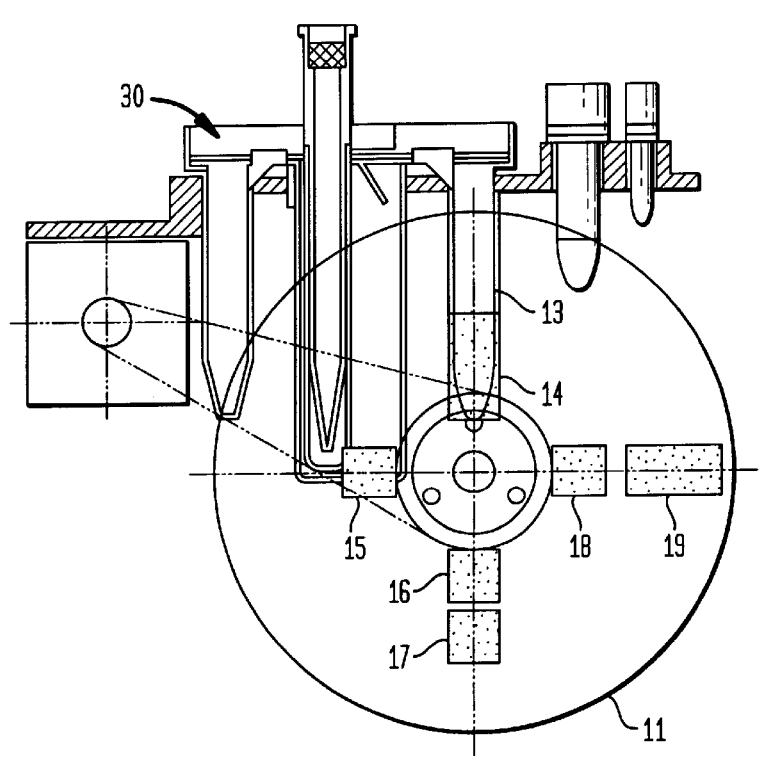
FIG. 1 is a schematic front view of a first embodiment of an apparatus according to the invention.
Figure 2:
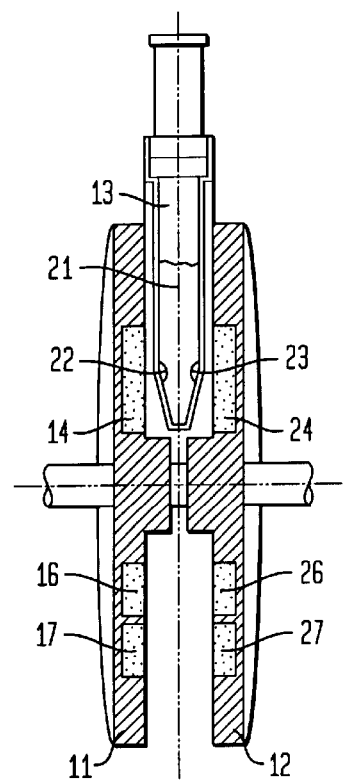
FIG. 2 is a side elevation of the apparatus according to FIG. 1.
Figure 3:
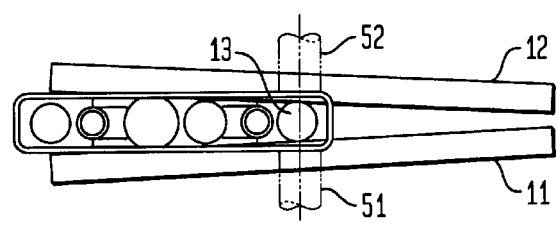
FIG. 3 is a plan view of the apparatus according to FIG. 1.

As shown by FIG. 1, the first array of magnet elements 14–19 comprises a first magnet element 14 and a second magnet element 15. These magnet elements are positioned on the carrier 11 at different distances from the rotation axis 51. Some of the magnet elements 14–19 lie on the same radius, e.g. magnet elements 18 and 19, and some of the magnet elements of the array lie on radii located at different azimuth angles, e.g. magnet element 14 and magnet element 15.

The carrier 11 and the array of magnet elements 14–19 are so configured and dimensioned that by rotation of carrier 11 one or more of the magnet elements of the first array of magnet elements 14–19 can be positioned close to the external surface of the side wall of the reaction vessel 13 on one side thereof.

The apparatus further comprises a motor and mechanical transmission means controlled by suitable control means for rotating and selectively positioning said carrier 11 and thereby said array of magnet elements 14–19 at a plurality of predetermined angular positions with respect to reaction vessel 13.

Figure 4:
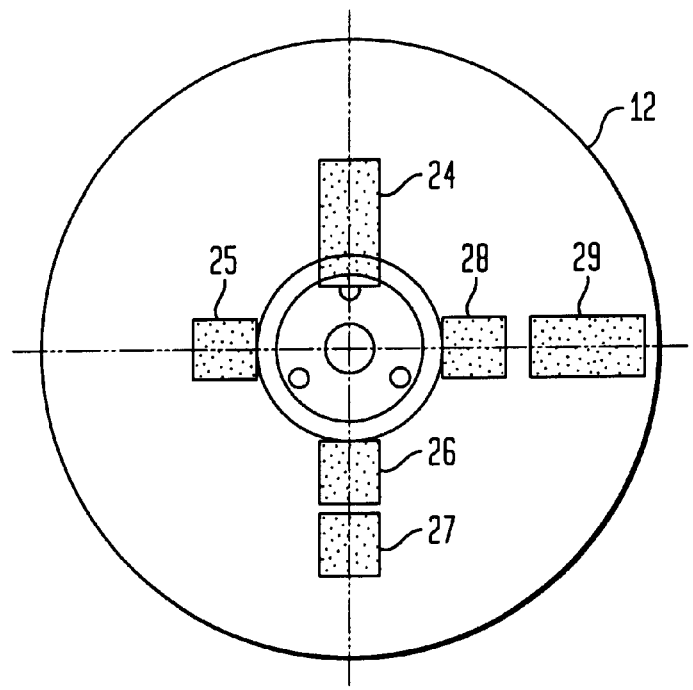
FIG. 4 is a front view of a first embodiment of an array of magnet elements held by carrier 12 in FIG. 1.

In a preferred embodiment the apparatus comprises a second carrier 12 holding a second array of magnet elements 24–29 shown by FIG. 4. Carrier 12 is rotatable about a rotation axis 52.

The above description of carrier 11 and array of magnet elements 14–19 also applies to carrier 12 and array of magnet elements 24–29, because both arrays of magnet elements are symmetrically arranged with respect to the longitudinal symmetry axis of reaction vessel, so that for each angular position of carriers 11, 12 identically configured magnet elements or arrays of magnet elements are positioned on opposite sides of reaction vessel 13.

Carriers 11, 12 are so connected with each other that rotation of one of the carriers of a predetermined angle causes rotation of the other carrier of the same angle.

Each of the magnet elements of the arrays of magnet elements 14–19 or 24–29 comprises one or more magnets having preferably the same width and the same azimuthal position on the carrier of the array.

The axis 51 of rotation of carrier 11 and the axis 52 of rotation of carrier 12 intersect with the length axis of reaction vessel 13 at a point located below the bottom of reaction vessel 13.

In the embodiment shown by FIGS. 1 to 4, the axis of rotation 51, 52 of the carriers 11, 12 form an angle which is in the range between 5 and 10 degrees This is preferred when reaction vessel 13 is part of a processing unit having a configuration that makes suitable to have such an angle between the rotation axis 51, 52. Otherwise an embodiment is preferred wherein the carriers have a common axis of rotation, as shown by carriers 62, 63 in FIG. 7b.

Second Embodiment

Figure 5:
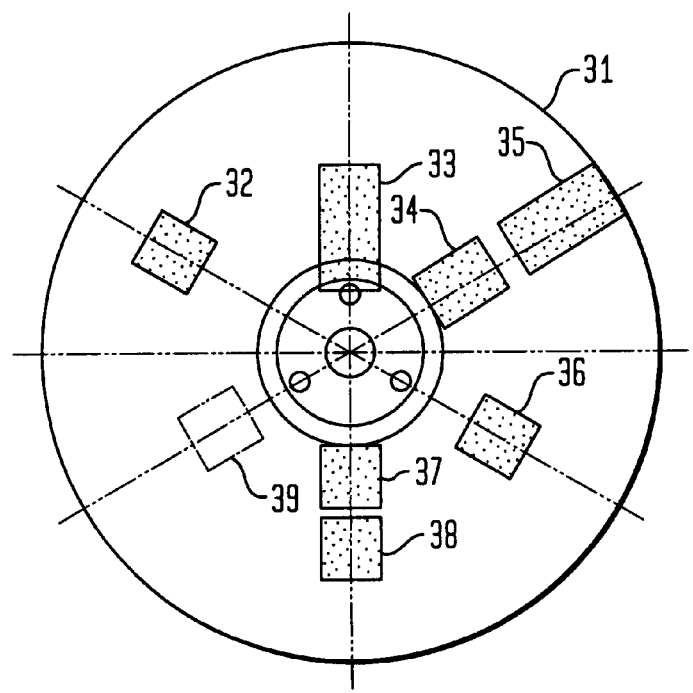
FIG. 5 is a front view of a second embodiment of an array of magnet elements held by carrier 12 in FIG. 1.

A second embodiment of an apparatus according to the invention is similar to the embodiment described with reference to FIGS. 1 to 4, but differs therefrom in that it comprises one or two carriers on each of which an array of magnets is mounted which differs from the arrays of magnets described with reference to FIGS. 1–4. A preferred array of magnets for this second embodiment of the apparatus is array of magnets 32–39 mounted on a carrier 31 as shown in FIG. 5.

Third Embodiment

A third embodiment of an apparatus according to the invention comprises magnet arrays shown by FIG. 6. The exploded view shown by this Figure shows a first carrier 42 which carries an array of magnet elements 54, 55, 56 and a second carrier 43 which carries an array of magnet elements 57, 58, 59. Carriers 42, 43 are connected with each other and with a driving wheel 49 by means of coupling elements 44, 45, a ring 47 and a disk 48. Coupling element 45 includes a shaft 46 driven by driving wheel 49. Driving wheel 49 is connected to a motor and suitable control means not shown in FIG. 6. By means of such motor and control means carriers 42, 43 can be rotated to a plurality of angular positions for positioning magnet elements on carrier 42 and/or carrier 43 close to the external surface of the side wall of a reaction vessel positioned between carriers 42, 43. The main difference between this third embodiment and the above described first and second embodiments is that in this third embodiment in some angular positions magnet elements can be asymmetrically positioned with respect to the reaction vessel. This permits angular positions where a magnet element is positioned only on one side of the reaction vessel, other angular positions where magnet elements are positioned on opposite sides of the reaction vessel, and also angular positions at which no magnet element is positioned close to the external surface of the side wall of the reaction vessel.

Fourth Embodiment

A fourth embodiment of an apparatus according to the invention is described hereinafter with reference to FIGS. 7a, 7b, 8a, 8b, etc. up to 20a, 20b.

FIG. 7a shows a front view of carriers 62, 63 which carry magnet arrays 71–75 and 81–85 respectively. FIG. 7b shows a side elevation view including a cross-section through planes indicated by lines A—A of the apparatus according to FIG. 7a and shows also a reaction vessel 13 positioned between carriers 62, 63.

Carriers 62, 63 are connected to a shaft 64 supported by bearings 66, 67. A coupling element 65 connects carriers 62 and 63 with each other. Shaft 64 is connected to motor and mechanical transmission means (not shown) controlled by suitable control means for rotating and selectively positioning said carriers 62, 63 and thereby the arrays of magnet elements mounted on them at a plurality of predetermined angular positions with respect to reaction vessel 13 positioned between carriers 62, 63.

FIGS. 7a, 7b and the figures following them show various angular positions of carriers 62, 63 and thereby various corresponding angular positions of the magnet arrays mounted thereon with respect to a reaction vessel 13 located at a predetermined stationary position between carriers 62, 63. FIGS. 7a, 7b and the figures following them illustrate in addition various processing steps carried out with respect to the contents of the reaction vessel 13.

Use of an Apparatus According to the Invention

Such a use is described hereinafter for carrying a process to isolate a nucleic acid from biological cell material with the fourth embodiment of an apparatus according to the invention described above with reference to FIGS. 7a and 7b. Such a process comprises the following steps illustrated by the Figures indicated between parentheses:

Step 1: Separation of Magnetic Particles (FIGS. 7a, 7b)

In this step carriers 62 and 63 have the angular position (Pos. 1) shown by FIG. 7a. FIG. 7b shows a cross-section through A—A in FIG. 7a. As shown by FIG. 7b, reaction vessel 13 contains a predetermined volume, e.g. 2.7 ml, of a lysing suspension 91 which contains biological cell material to be lysed and magnetic particles used as solid phase in a process for isolating nucleic acid contained in said cell material. Magnets 71 and 81 located on opposite sides of and close to the external surface of the side wall of reaction vessel 13 attract magnetic particles contained in lysing suspension 91 towards the inner surface of the side wall of reaction vessel 13. In this way the magnetic particles are grouped in layers deposited on opposite sides 92, 93 of the inner surface of the side wall of reaction vessel 13.

Step 2: Aspiration of Lysing Suspension (FIGS. 8a, 8b)

As shown by FIG. 8a, in this step carriers 62 and 63 have the same angular position (Pos. 1) as in step 1. FIG. 8b shows a cross-section through A—A in FIG. 8a. In this step 2 lysing suspension 91 is aspirated from reaction vessel 13 e.g. by means of an automatic pipettor, and as shown by FIG. 8b a layer of magnetic particles remains held on each of the opposite sides 92, 93 of the inner surface of the side wall of reaction vessel 13 by action of magnetic force exerted on those particles by magnets 71 and 81.

Step 3: Dispensing of a First Wash Buffer (FIGS. 9a, 9b)

As shown by FIG. 9a, in this step carriers 62 and 63 have the same angular position (Pos. 1) as in steps 1 and 2. FIG. 9b shows a cross-section through A—A in FIG. 9a. A predetermined volume, e.g. 2.8 ml, of a first wash buffer 94 is introduced in reaction vessel 13, and as shown by FIG. 9b layers of magnetic particles remain held on the inner surface of sides 92, 93 of the side wall of reaction vessel 13 by magnetic force exerted on those particles by magnets 71 and 81.

Step 4a: Washing of Magnetic Particles (FIGS. 10a, 10b)

Figure 10A:
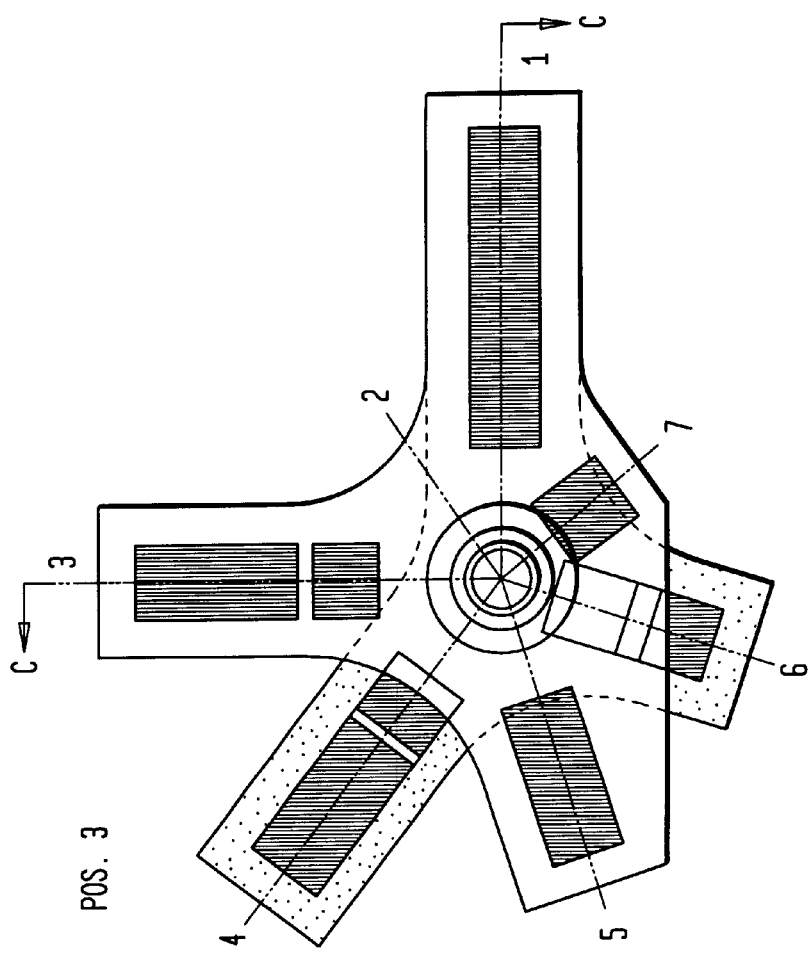
Figure 10B:
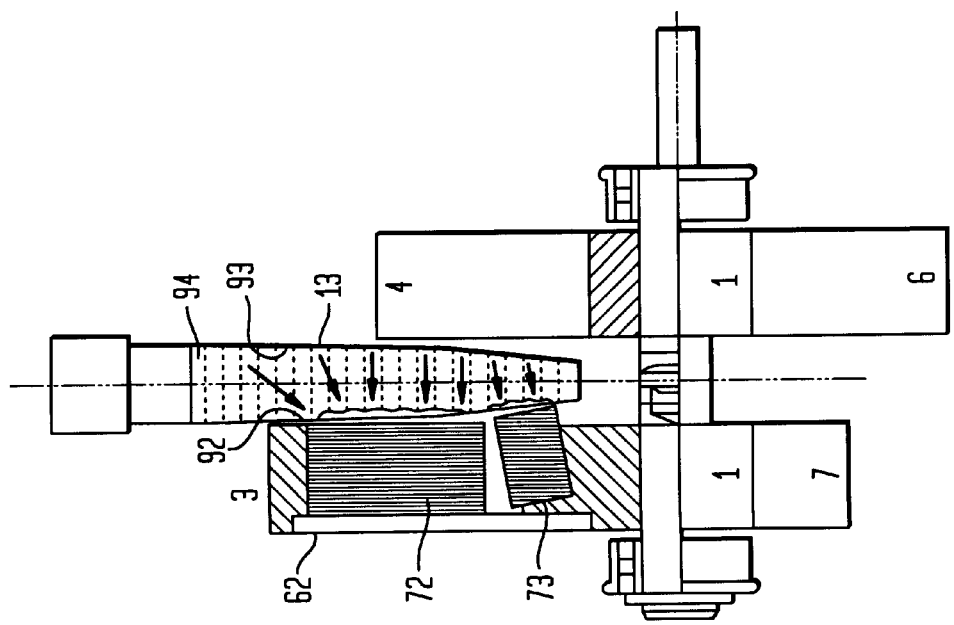

In this step carriers 62 and 63 have the angular position (Pos. 3) shown by FIG. 10a. FIG. 10b shows a cross-section through C—C in FIG. 10a. As shown by FIG. 10b, in this step 4a magnets 72, 73 mounted on carrier 62 and located close to the external surface of the side wall of reaction vessel 13 hold the magnetic particles located on side 92 of the inner surface of the side wall of the reaction vessel 13 and attract the layer of magnetic particles located on the opposite side of the inner surface of the side wall of the reaction vessel 13. The latter particles are thereby moved through wash buffer 94 and join the magnetic particles of the layer which lie on the opposite side 92 of the inner surface of the side wall of reaction vessel 13. In this way the magnetic particles of layer which are moved from side 93 to the opposite side 92 get washed by wash buffer 94. At the end of this step 4a all magnetic particles are grouped in a layer on side 92 of the inner surface of the side wall of reaction vessel in a region close to magnets 72, 73.

Step 4b: Washing of Magnetic Particles (FIGS. 11a, 11b)

In this step carriers 62 and 63 have the angular position (Pos. 4) shown by FIG. 11a. FIG. 11b shows a cross-section through D—D in FIG. 11a. As shown by FIG. 11b, in this step 4b magnets 82, 83 mounted on carrier 63 and located close to the external surface of the side wall of reaction vessel 13 move the magnetic particles from side 92 of the inner surface of the side wall of the reaction vessel 13 to the opposite side 93 of the inner surface of the side wall of the reaction vessel 13. The magnetic particles are moved through the first wash buffer 94 and get thereby washed by this wash buffer. At the end of this step 4b all magnetic particles are grouped in a layer on side 93 of the inner surface of the side wall of reaction vessel in a region close to magnets 82, 83.

Steps 4a and 4b are repeated e.g. 3 times.

Step 5: Separation of Magnetic Particles to Low Level (FIGS. 12a, 12b)

Figure 12A:
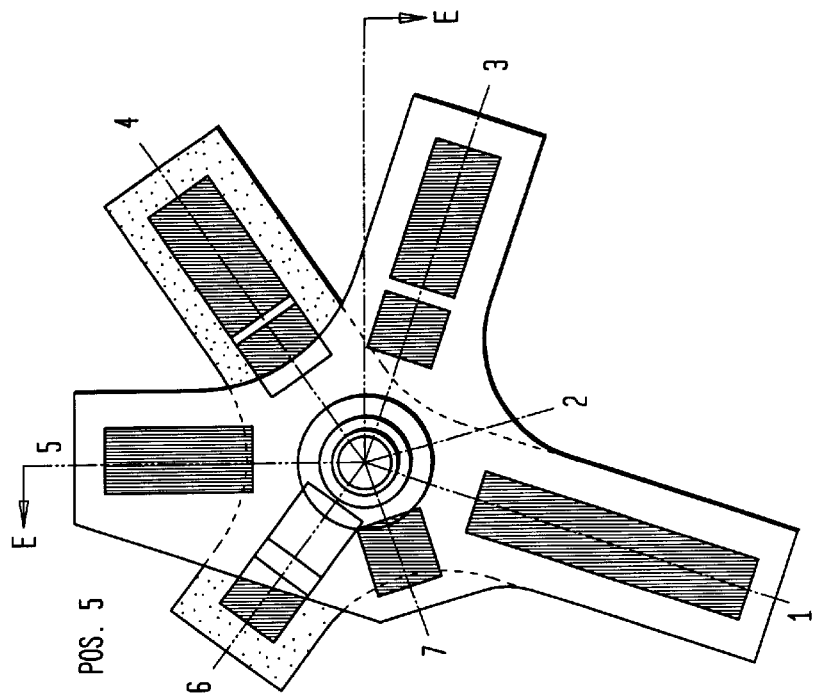
Figure 12B:
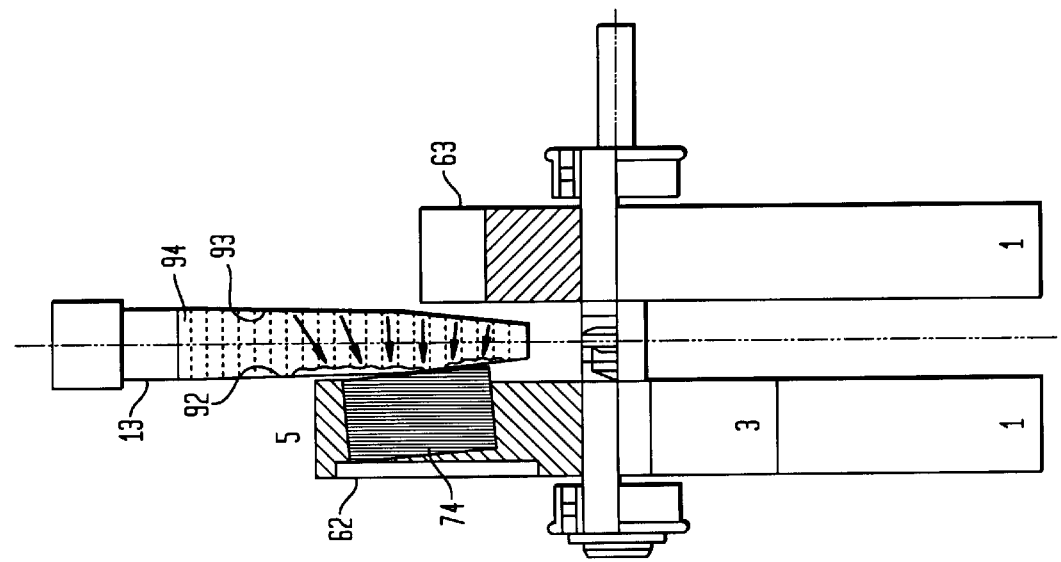

In this step carriers 62 and 63 have the angular position (Pos. 5) shown by FIG. 12a. FIG. 12b shows a cross-section through E—E in FIG. 12a. As shown by FIG. 12b, in this step 5a magnet 74 mounted on carrier 62 and located close to the lower part of the external surface of the side wall of reaction vessel 13 moves the magnetic particles from side 93 of the inner surface of the side wall of the reaction vessel 13 to the lower part of the opposite side 92 of the inner surface of the side wall of the reaction vessel 13.

Step 6: Aspiration of Wash Buffer (FIGS. 13a, 13b)

As shown by FIG. 13a, in this step carriers 62 and 63 have the same angular position (Pos. 5) as in step 5. FIG. 13b shows a cross-section through E—E in FIG. 13a. In this step 6 the first wash buffer 94 is aspirated from reaction vessel 13 e.g. by means of an automatic pipettor, and as shown by FIG. 13b a layer 95 of magnetic particles remains held on the lower part of side 92 of the inner surface of the side wall of reaction vessel 13 by action of magnetic force exerted on those particles by magnet 74 mounted on carrier 62.

Step 7: Dispensing of Wash Buffer (FIGS. 14a, 14b)

Figure 14A:
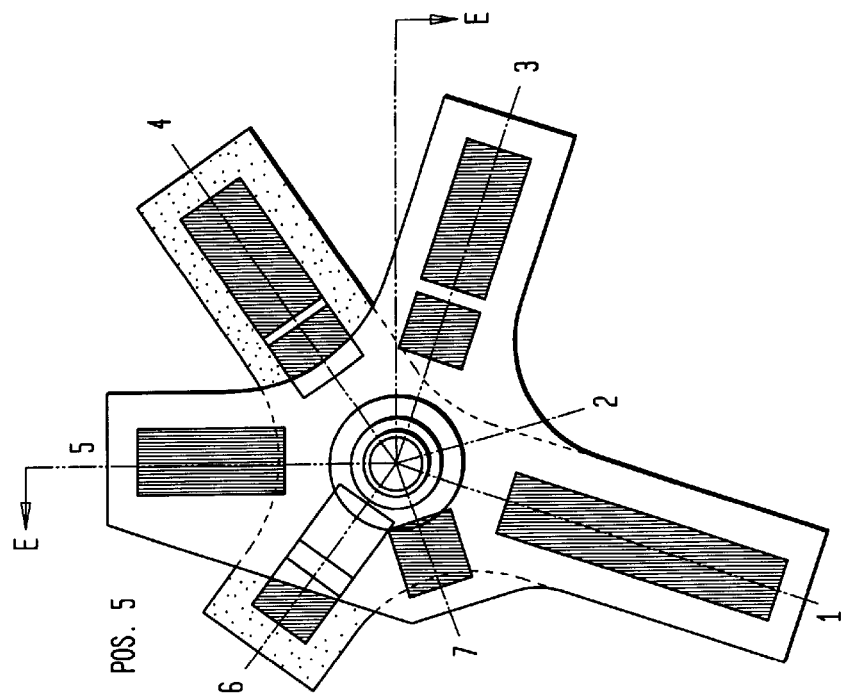
Figure 14B:
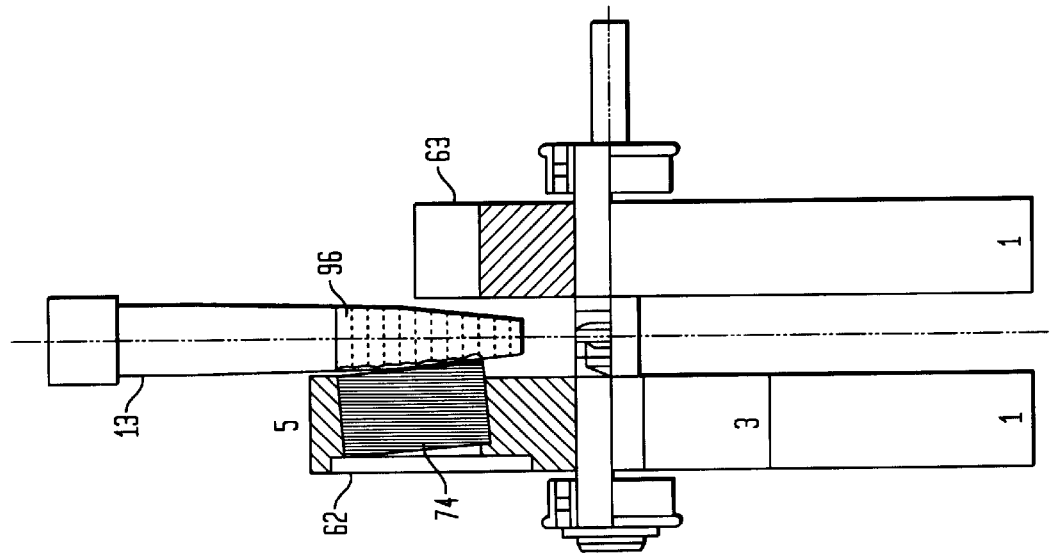

As shown by FIG. 14a, in this step carriers 62 and 63 have the same angular position (Pos. 5) as in steps 5 and 6. FIG. 14b shows a cross-section through E—E in FIG. 14a. In this step 7 a predetermined volume, e.g. 1 ml, of a second wash buffer 96 is introduced in reaction vessel 13, and as shown by FIG. 14b a layer 95 of magnetic particles remains held on the inner surface of sides 92 of the side wall of reaction vessel 13 by magnetic force exerted on those particles by magnet 74 mounted on carrier 62.

Step 8a: Washing of Magnetic Particles (FIGS. 15a, 15b)

In this step carriers 62 and 63 have the angular position (Pos. 5) shown by FIG. 15a. FIG. 15b shows a cross-section through E—E in FIG. 15a. As shown by FIG. 15b, in this step 8a magnet 74 mounted on carrier 62 and located close to the external surface of the side wall of reaction vessel 13 holds the magnetic particles located on the lower part of side 92 of the inner surface of the side wall of the reaction vessel 13. At the end of this step 8a all magnetic particles are grouped in a layer on side 92 of the inner surface of the side wall of reaction vessel in a region close to 74.

Step 8b: Washing of Magnetic Particles (FIGS. 16a, 16b)

Figure 16A:
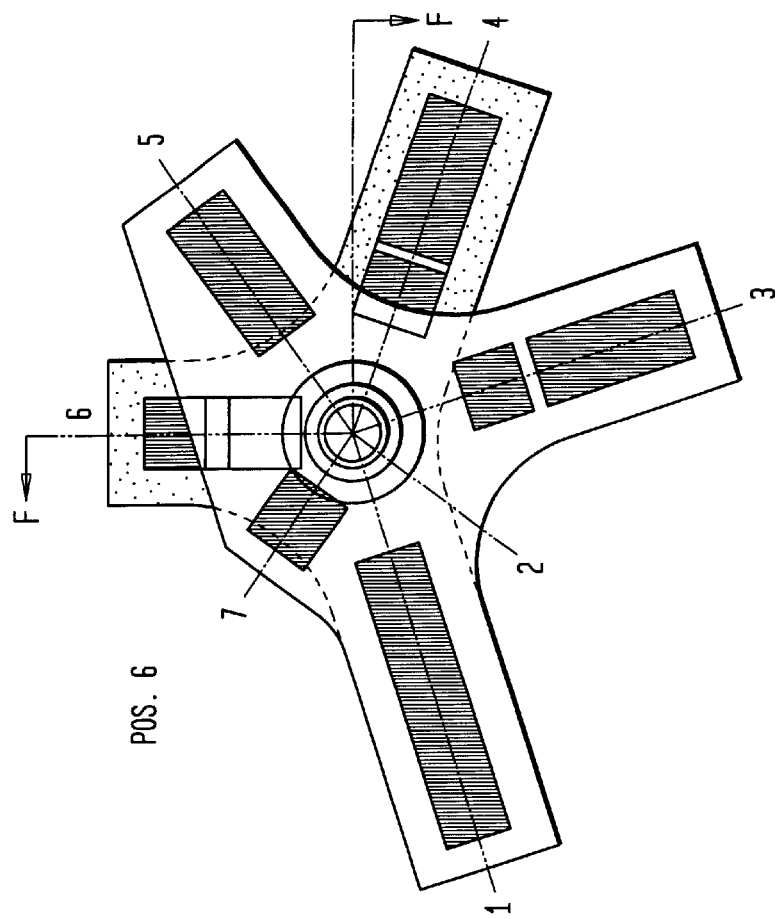
Figure 16B:
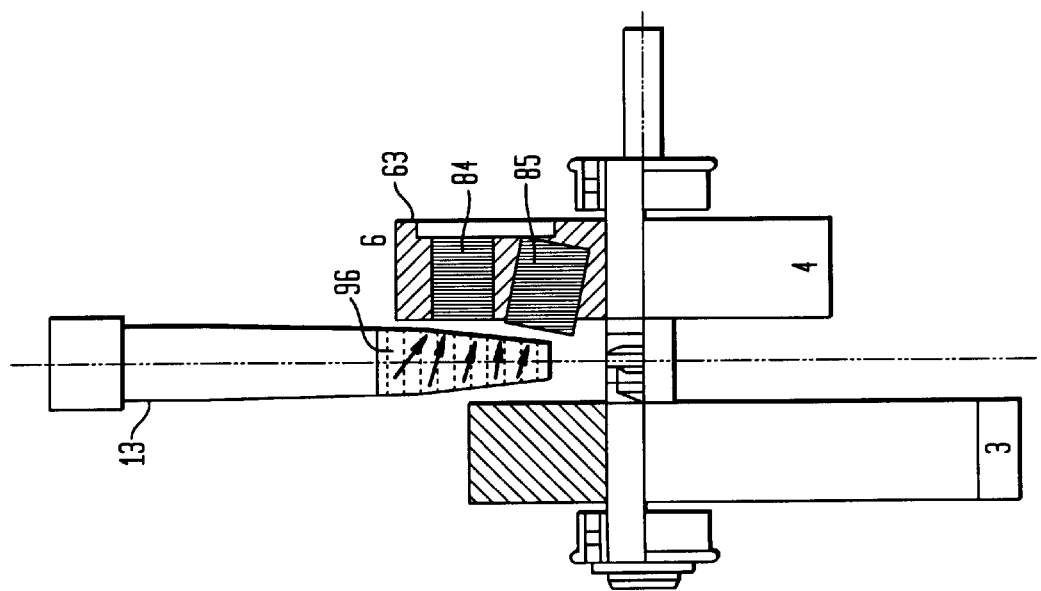

In this step carriers 62 and 63 have the angular position (Pos. 6) shown by FIG. 16a. FIG. 16b shows a cross-section through F—F in FIG. 16a. As shown by FIG. 16b, in this step 8b magnets 84, 85 mounted on carrier 63 and located close to the external surface of the side wall of reaction vessel 13 move the magnetic particles from the lower part of side 92 to the lower part of opposite side 93 of the inner surface of the side wall of the reaction vessel 13. The magnetic particles are moved through wash buffer 96 and get thereby washed by this wash buffer. At the end of this step 8b all magnetic particles are grouped in a layer on the lower part of side 93 of the inner surface of the side wall of reaction vessel 13 in a region close to magnets 84, 85.

Steps 8a and 8b are repeated e.g. 3 times.

Step 9: Separation of Magnetic Particles to Low Level (FIGS. 17a, 17b)

In this step carriers 62 and 63 have the angular position (Pos. 7) shown by FIG. 17a. FIG. 17b shows a cross-section through G—G in FIG. 17a. As shown by FIG. 17b, in this step 9 magnet 75 mounted on carrier 62 and located close to the external surface of the side wall of reaction vessel 13 moves the magnetic particles from the lower part of side 93 to the lowest part of the opposite side 92 of the inner surface of the side wall of the reaction vessel 13.

Step 10: Aspiration of Wash Buffer (FIGS. 18a, 18b)

As shown by FIG. 18a, in this step carriers 62 and 63 have the same angular position (Pos. 7) as in step 9. FIG. 18b shows a cross-section through G—G in FIG. 18a. In this step 10 the second wash buffer 96 is aspirated from reaction vessel 13 e.g. by means of an automatic pipettor, and as shown by FIG. 18b a layer 97 of magnetic particles remains held on the lowest part of side 92 of the inner surface of the side wall of reaction vessel 13 by action of magnetic force exerted on those particles by magnet 75 mounted on carrier 62.

Step 11: Release of Pellets (FIGS. 19a, 19b)

In this step carriers 62 and 63 have the angular position (Pos. 6) shown by FIG. 19a. FIG. 19b shows a cross-section through F—F in FIG. 19a. As shown by FIG. 19b, in this step 11 magnets 84, 85 mounted on carrier 63 and located close to the external surface of the side wall of reaction vessel 13 release pellets which form layer 97 of magnetic particles by moving them from the lowest part of side 92 to the lowest part of side 93 of the inner surface of the side wall of the reaction vessel 13.

Step 12: Addition of Specimen Diluent (FIGS. 20a, 20b)

Figure 20A:
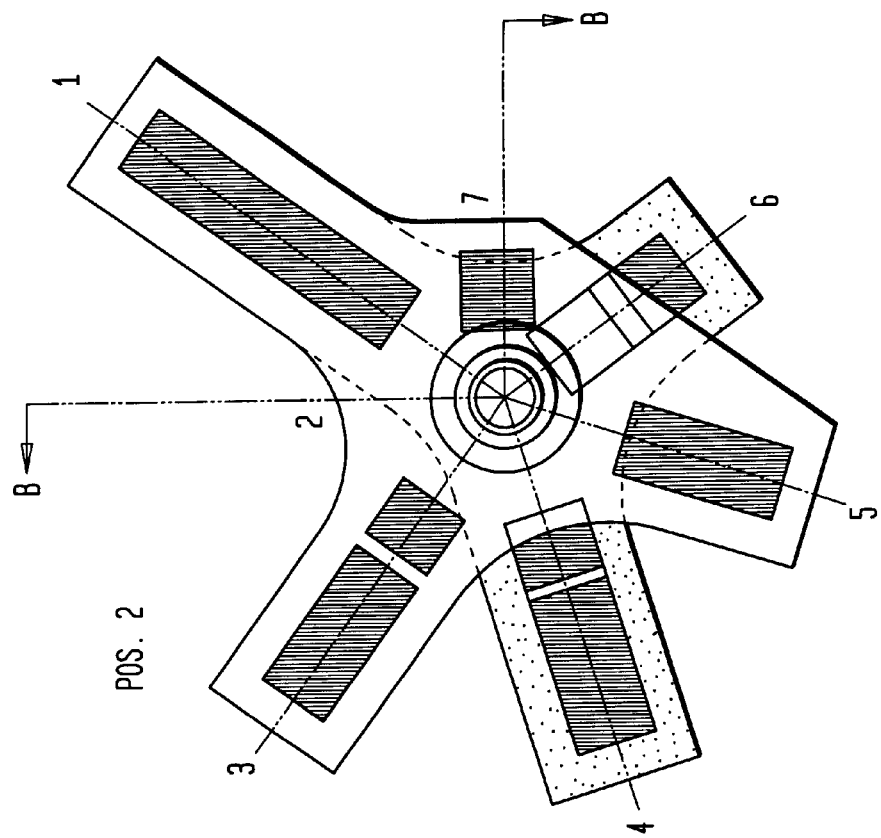
Figure 20B:
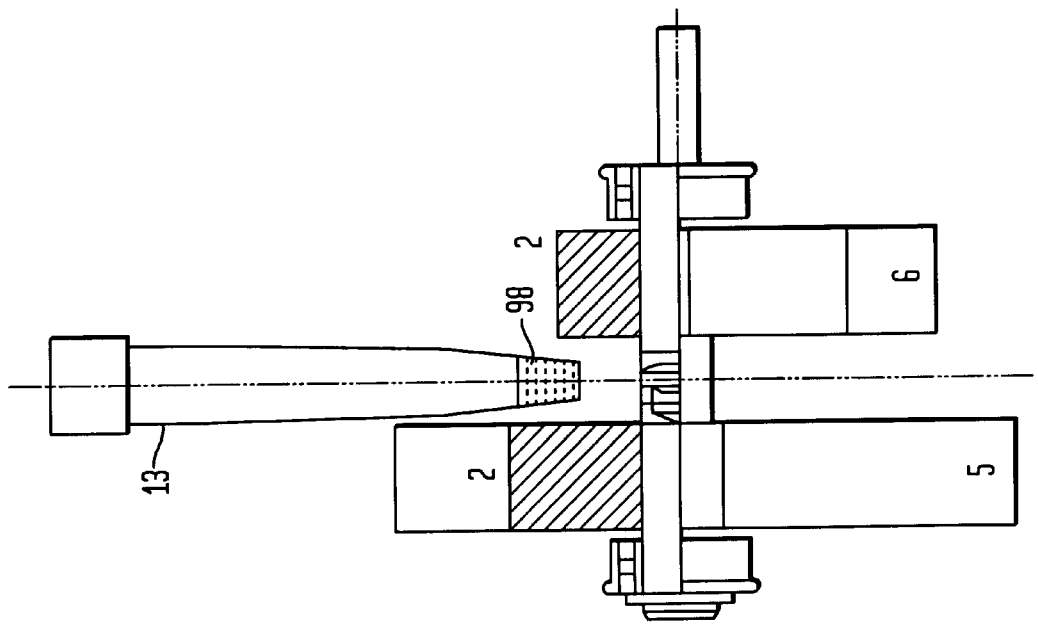

In this step carriers 62 and 63 have the angular position (Pos. 2) shown by FIG. 20a. FIG. 20b shows a cross-section through B—B in FIG. 20a. As shown by FIG. 20b, in this step 12 none of the magnets mounted on carriers 62 and 63 are located close to the external surface of the side wall of reaction vessel 13. A predetermined volume of specimen diluent 98 is dispensed into reaction vessel 13.

Step 13: Mixing of Magnet Particles in Reaction Vessel (FIGS. 21a, 21b)

As shown by FIG. 21a, in this step carriers 62 and 63 have the same angular position (Pos. 2) as in step 12. FIG. 21b shows a cross-section through B—B in FIG. 21a. In this step 13, by means of a so called titration step the magnet particles present in the suspension contained in the reaction vessel 13 are thoroughly mixed by repeatedly aspirating said liquid from the vessel and redispensing it into the reaction vessel, e.g. by means of an automatic pipettor. This aspirating and redispensing is suggested in FIG. 21b by arrows pointing in opposite senses. At the end of step 13 reaction vessel contains a sample containing nucleic acid extracted from the biological cell material contained in the primary sample contained in reaction vessel 13 at the beginning of step 1. The nucleic acid sample present in reaction vessel 13 at the end of step 13 can be used e.g. for carrying out a polymerase chain reaction to amplify said nucleic acid.

Supplementary Description of Above Described Embodiments

A common feature of the above described embodiments is that the means for selectively positioning the carrier or carriers which hold the magnet elements are adapted to position said carrier or carriers at predetermined angular positions which are selected according to a processing step to be carried out in that reaction vessel 13 and/or according to the amount of liquid in the reaction vessel 13.

As described above with reference to embodiments 3 and 4 at some of the predetermined angular positions of the carrier or carriers of magnet elements one or more magnet elements can be positioned close to the external surface of only one side of the reaction vessel 13, whereas in other of such predetermined angular positions one or more magnet elements can be positioned close to the external surface of the reaction vessel 13 on one side thereof and also close to the external surface of the reaction vessel on the opposite side thereof. As described above in particular with reference to embodiment 4 at least one of the predetermined angular positions of the carrier or carriers of magnet elements can be a position at which no magnet element is located close to any external surface of the reaction vessel 13.

In all above described embodiments of an apparatus according to the invention: each of the magnet elements of said array or arrays of magnet elements preferably comprises one or more magnets having the same width and the same azimuthal position on the carrier of the array; and, the axis of rotation of the carrier, respectively of each of the carriers, preferably intersects with the length axis of the reaction vessel at a point located below the bottom of the reaction vessel.

In embodiments comprising two carriers of arrays of magnet elements, these carriers have preferably a common axis of rotation.

In all above described embodiments of an apparatus according to the invention the apparatus comprises a motor and mechanical transmission means controlled by suitable control means for rotating and selectively positioning the carrier and thereby said array of magnet elements at a plurality of predetermined angular positions with respect to reaction vessel. Such control means preferably include means which perform the necessary control in response to commands provided by a process control unit which controls the processing of a sample-reagent mixture being processed in the reaction vessel. All control means just mentioned can be e.g. part of a control unit of an automatic apparatus. Such control means can include hardware and software means.

What is claimed is:

1. Apparatus for separating magnetic particles in suspension in a fluid, said apparatus comprising a first carrier holding a plurality of first magnetic elements at different locations on said first carrier;

a second carrier offset from said first carrier and holding a plurality of second magnetic elements at different locations on said second carrier, said first and second carriers defining a region therebetween;

each of at least one of said first magnetic elements being disposed across said region from a corresponding one of said second magnetic elements, at least one other one of said first magnetic elements not being disposed across said region from any magnetic element on said second carrier, and at least one another one of said second magnetic elements not being disposed across said region from any magnetic element on said first carrier;

means for holding a reaction vessel containing said suspended magnetic particles in said region; and means for providing relative motion between said carriers and said holding means.

2. The apparatus of claim 1 wherein said means for providing relative motion rotates said first and said second carriers respectively about first and second axes.

3. The apparatus of claim 2 wherein said at least one other one of said first magnetic elements includes two magnetic elements disposed at different distances from the rotational axis of said first carrier.

4. The apparatus of claim 2 wherein said at least one other one of said first magnetic elements includes two magnetic elements lying on radii located at different azimuth angles.

5. The apparatus of claim 2 wherein said at least one another one of said second magnetic elements includes two magnetic elements disposed at different distances from the rotational axis of said second carrier.

6. The apparatus of claim 2 wherein said at least one other one of said first magnetic elements includes two magnetic elements lying on radii located at different azimuth angles.

7. The apparatus of claim 2 wherein the rotational axes of said first and second carriers are collinear.

8. The apparatus of claim 2 wherein the rotational axis of said first and second carriers form a nonzero angle therebetween.

9. Apparatus for separating magnetic particles in suspension in a fluid, said apparatus comprising a first carrier holding a plurality of first magnetic elements at different locations on said first carrier;

a second carrier offset from said first carrier and holding a plurality of second magnetic elements at different locations on said second carrier, said first and second carriers defining a region therebetween, one of said first magnetic elements being disposed across said region from one of said second magnetic elements, at least one of said first magnetic elements not being disposed across said region from any magnetic element on said second carrier, and at least one another one of said second magnetic elements not being disposed across said region from any magnetic element on said first carrier;

a reaction vessel containing said suspended magnetic particles in said region; and means for providing relative motion between said carriers and said holding means.

10. The apparatus of claim 9 wherein said means for providing relative motion rotates said first and said second carriers respectively about first and second axes.

11. The apparatus of claim 10 wherein said at least one other one of said first magnetic elements includes two magnetic elements disposed at different distances from the rotational axis of said first carrier.

12. The apparatus of claim 10 wherein said at least one other one of said first magnetic elements includes two magnetic elements lying on radii located at different azimuth angles.

13. The apparatus of claim 10 wherein said at least one another one of said second magnetic elements includes two magnetic elements disposed at different distances from the rotational axis of said second carrier.

14. The apparatus of claim 10 wherein said at least one another one of said second magnetic elements includes two magnetic elements lying on radii located at different azimuth angles.

15. The apparatus of claim 10 wherein the rotational axes of said first and second carriers are collinear.

16. The apparatus of claim 10 wherein the rotational axis of said first and second carriers form a nonzero angle therebetween.

17. Apparatus for separating magnetic particles in suspension in a fluid, said apparatus comprising:

a first carrier rotatable about an first axis, said first carrier having a first plurality of magnetic elements positioned along different radii of said first carrier;

a second carrier rotatable about a second axis and offset from said first carrier by a gap, said second carrier having a second plurality of magnetic elements positioned along different radii of said second carrier, one magnetic element of said second plurality of magnetic elements having a corresponding magnetic element of said first plurality of magnetic elements located across said gap from said one magnetic element, and another magnetic element of said second plurality of magnetic elements having no corresponding magnetic element located axially across said gap from said another magnetic element; and means for positioning an elongated vessel having a longitudinal axis within said gap so that said longitudinal axis lies on a plane, generally perpendicular to said first and second axes of rotation.

* * * * *